US008460387B2

(12) United States Patent
Theofilos (10) Patent No.: US 8,460,387 B2
(45) Date of Patent: Jun. 11, 2013

(54) INTERVERTEBRAL IMPLANT AND FACE PLATE COMBINATION

(75) Inventor: Charles Theofilos, Palm Beach Gardens, FL (US)

(73) Assignee: Spartan Cage, LLC, Palm Beach Gardens, FL (US)

( * ) Notice: Subject to any disclaimer, the term of this patent is extended or adjusted under 35 U.S.C. 154(b) by 0 days.

(21) Appl. No.: 13/154,169

(22) Filed: Jun. 6, 2011

(65) Prior Publication Data

US 2011/0301713 A1 Dec. 8, 2011

Related U.S. Application Data

(60) Provisional application No. 61/351,676, filed on Jun. 4, 2010.

(51) Int. Cl.
*A61F 2/44* (2006.01)
*A61B 17/70* (2006.01)

(52) U.S. Cl.
USPC .......................... 623/17.16; 606/246; 606/279

(58) Field of Classification Search
USPC ....... 606/246, 249, 279, 301, 105; 623/17.11, 623/17.16
See application file for complete search history.

(56) References Cited

U.S. PATENT DOCUMENTS

| 6,322,562 | B1 | 11/2001 | Wolter |
| 6,342,074 | B1 | 1/2002 | Simpson |
| 2008/0021555 | A1 | 1/2008 | White et al. |
| 2008/0051890 | A1 | 2/2008 | Waugh et al. |
| 2010/0217393 | A1 | 8/2010 | Theofilos |
| 2010/0305704 | A1 | 12/2010 | Messerli et al. |
| 2010/0312346 | A1 | 12/2010 | Kueenzi et al. |
| 2010/0324683 | A1 | 12/2010 | Reichen et al. |
| 2011/0040382 | A1 | 2/2011 | Muhanna |

FOREIGN PATENT DOCUMENTS

| WO | WO 2006/066228 A2 | 6/2006 |
| WO | WO 2010/054208 A1 | 5/2010 |

OTHER PUBLICATIONS

International Search Report and Written Opinion of the International Searching Authority mailed Sep. 29, 2011 in counterpart International Application No. PCT/US2011/039291 filed Jun. 6, 2011.

*Primary Examiner* — Eduardo C Robert
*Assistant Examiner* — David Comstock
(74) *Attorney, Agent, or Firm* — Carter, DeLuca, Farrell & Schmidt, LLP (57) ABSTRACT

An intervertebral implant assembly includes an implant member and a retention member. The implant member includes a body portion and an attaching portion. The body portion includes first and second surfaces adapted to engage first and second vertebral bodies, respectively. The attaching portion defines a first guide portion that leads into the first surface. The retention member is detachably coupled to the attaching portion of the implant member. In particular, the attaching portion of the implant member is at least partially disposed in the retention member. The retention member defines an access bore configured and dimensioned to receive a bone screw therein. The access bore is in communication with the first guide portion, whereby when the bone screw is inserted through the access bore the bone screw is directed to the first vertebral body through the first guide portion.

26 Claims, 8 Drawing Sheets

INTERVERTEBRAL IMPLANT AND FACE PLATE COMBINATION

CROSS-REFERENCE TO RELATED APPLICATION

This application claims priority to, and the benefit of, U.S. Provisional Patent Application No. 61/351,676, filed on Jun. 4, 2010, the entire contents of which are hereby incorporated by reference herein.

BACKGROUND

1. Technical Field

The present disclosure relates to an apparatus for treating spinal conditions, and more particularly, to an intervertebral implant and a method of use therefor.

2. Background of Related Art

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two winglike projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as inter-vertebral discs. Inter-vertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the inter-vertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the inter-vertebral discs. Corpectomy involves removal of the vertebral body as well as the adjacent inter-vertebral discs.

A number of spinal surgical devices may be used to promote bony fusion after decompressing the spinal nerves. For instance, surgeons often replace the diseased vertebral tissue with one or more spinal cages and bone support matrix. Spinal cages support adjacent vertebral segments, while furthering spinal fusion of adjacent vertebral bodies. Scientists and clinicians have developed a number of devices and methods for decompressing spinal nerves. Improvements to this methods and devices are nevertheless still possible.

Furthermore, intervertebral spacer implants used as a stand-alone device or provided in an assembly including a retention mechanism to help alleviate expulsion and movement of the implant when placed in the spine, are well known. Such implant assemblies are advantageous in providing an implant that is easier to insert in the spine. Intervertebral spacer implant assemblies which include a spacer and a plate, where the plate comprises a supplemental or alternative retention mechanism having one or more holes in the anterior end of the plate that are directed toward the superior, inferior or both end plates of adjacent vertebrae are also known in the art. Such implants are used to stabilize and immobilize the spinal segments in the treatment of single or multi-level degenerative disc disease, spinal stenosis, and failed previous fusions, as well as other spine conditions.

One problem with such prior art devices is that they are not designed to enable the surgeon to place multiple bone screws within a single entry point in such a manner that they can be targeted for both the superior and inferior vertebral bodies surrounding the implant. A further deficiency in the prior art is that often times screws will loosen and be subject to falling out and presenting a dangerous situation for the patient. Accordingly, a need exists for an implant assembly that can safely and effectively stabilize the vertebral bodies.

SUMMARY

In accordance with an embodiment of the present disclosure, there is provided an intervertebral implant assembly including an implant member and a retention member. In particular, the implant member includes a body portion and an attaching portion. The body portion includes first and second surfaces adapted to engage first and second vertebral bodies, respectively. The attaching portion defines a first guide portion that leads into the first surface. In addition, the retention member is detachably coupled to the attaching portion of the implant member. In particular, the attaching portion of the implant member is at least partially disposed in the retention member. The retention member defines an access bore configured and dimensioned to receive a bone screw therein. The access bore is in communication with the first guide portion, whereby when the bone screw is inserted through the access bore the bone screw is directed to the first vertebral body through the first guide portion.

The access bore may be defined by arcuate and dished curvilinear sidewalls. The attaching portion may further define a second guide portion. The first and second guide portions may lead into the first and second surfaces, respectively. The access bore may be adapted and dimensioned to receive a pair of bone screws therein, whereby the pair of bone screws is inserted into the first and second vertebral bodies through the first and second guide portions, respectively. Head portions of the pair of bone screws may lockingly engage each other in the access bore. The first and second guide portions may each be defined in a peripheral portion of the attaching member.

In an embodiment, the intervertebral implant assembly may further include a pair of bone screws, wherein the access bore is adapted and dimensioned to receive the pair of bone screws. One of the pair of bone screws inserted through the access bore may be secured to the first vertebral body through the first guide portion, and the other of the pair of bone screws may be secured to the second vertebral body through the second guide portion.

The bone screw may include thread below a seat surface of the bone screw, whereby the thread deforms a portion of the sidewall of the access bore. The body portion may be tapered along the length thereof. The first and second surfaces may define projections to aid in securing the implant assembly between the vertebral bodies. In addition, the body portion may define a cavity.

Furthermore, the attaching portion of the implant member may define a male dovetail joint. The retention member may define a female dovetail joint corresponding to the male dovetail joint of the attaching portion. The first guide portion may be defined in the male dovetail joint of the attaching portion of the implant member. The first guide portion may lead into the first surface. The attaching portion of the implant member may further define second and third guide portions adjacent the male dovetail joint. The second and third guide portions may lead into the second surface. The retention member may further define a plurality of access bores corresponding to the first, second and third guide portions of the implant member.

The implant member may further include first and second sidewalls. The male dovetail joint may extend along the width of the implant member between the first and second sidewalls. The female dovetail joint may be defined along the length of the retention member. The female dovetail joint may correspond to the male dovetail joint disposed between the first and second sidewalls of the implant member. In addition, the intervertebral implant assembly may further include a retention clip disposed within the access bore of the retention member to retain the bone screws therein.

In accordance with another aspect of the present disclosure, there is provided a method of securing adjacent vertebral bodies. The method includes providing an intervertebral implant assembly. In particular, the implant assembly includes an implant member and a retention member. The implant member includes a body portion and an attaching portion. The body portion includes first and second surfaces adapted to engage first and second vertebral bodies, respectively. The attaching portion defines first and second guide portions that lead into the first and second surfaces, respectively. The retention member is detachably coupled to the attaching portion of the implant member. The retention member defines an access bore configured and dimensioned to receive therein a pair of bone screws. The access bore is in communication with the first and second guide portions, whereby when the pair of bone screws is inserted through the access bore the pair of bone screws is directed to the first and second vertebral bodies by the first and second guide portions.

The method further includes distracting adjacent vertebral bodies, inserting the intervertebral implant assembly between the first and second vertebral bodies and inserting the pair of bone screws through the retention member and into the respective vertebral bodies.

In an embodiment, the method may further include removing vertebral tissue. In addition, inserting the pair of bone screws through the retention member and into the respective vertebral bodies may include inserting the pair of bone screws through the access bore and into the first and second vertebral bodies through the first and second guide portions, respectively. The intervertebral implant assembly may further include a retainer clip disposed within the access bore. The retainer clip may have a bent open eight shape.

BRIEF DESCRIPTION OF THE DRAWINGS

Various embodiments of the present disclosure are described hereinbelow with reference to the drawings, wherein.

DETAILED DESCRIPTION OF EMBODIMENTS

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

Figure 1:
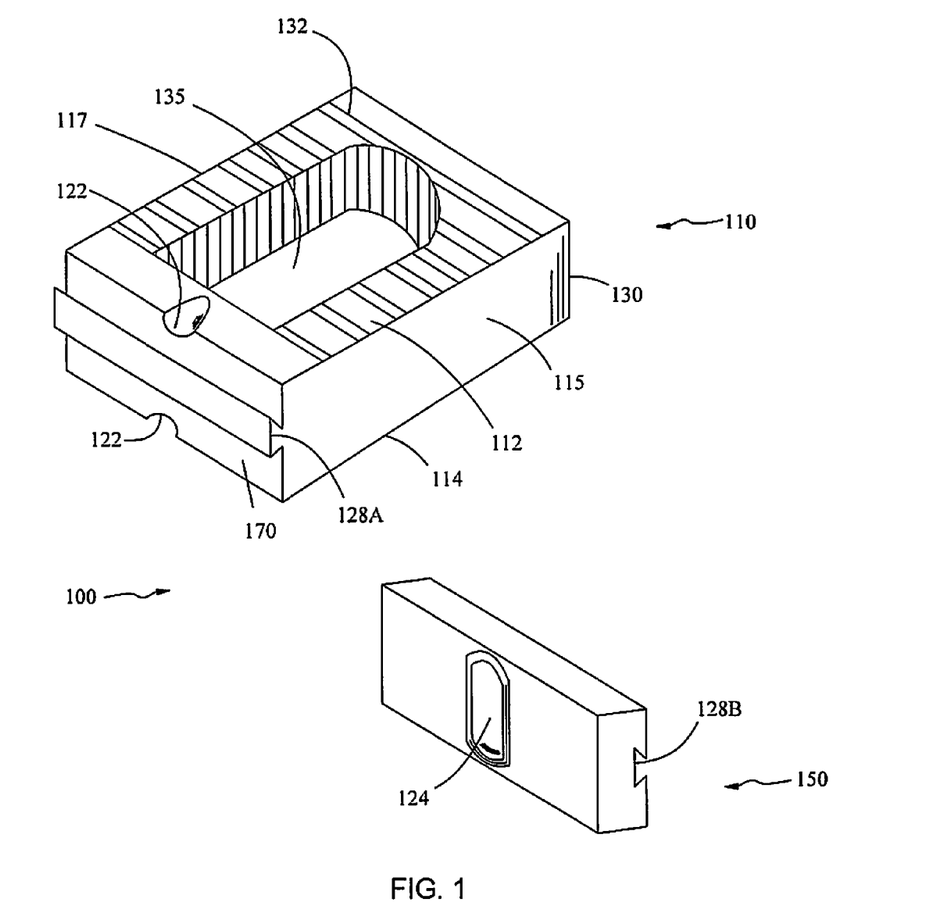
FIG. 1 is a perspective view of an intervertebral implant assembly in accordance with an embodiment of the present disclosure with parts separated.

With reference to FIG. 1, an embodiment of the present disclosure is shown generally as an intervertebral implant assembly 100 configured and adapted to be positionable between vertebral bodies 50, 52 (FIG. 2) to support vertebral bodies 50, 52 and to promote spinal fusion. Intervertebral implant assembly 100 includes an implant member 110 and a retention member 150. Implant member 110 and retention member 150 may be made of titanium, titanium alloy, stainless steel, allograft bone, autologous bone graft, polyetheretherketone (PEEK), cobalt chrome, polymeric materials, a combination thereof, or any other suitable biocompatible material. In particular, implant member 110 may be formed of bone, or an artificial material other than bone which may be harder or stronger than bone, such as, e.g., ceramic materials. Implant member 110 may include a bone growth promoting material such as, e.g., bone morphogenic protein and hydroxyapatite.

Figure 2:
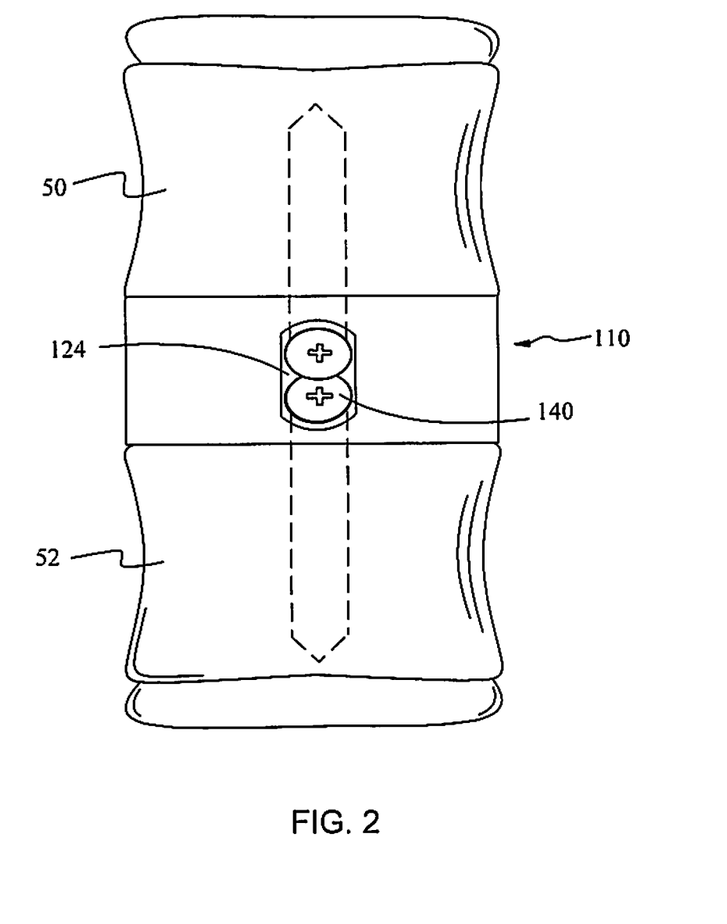
FIG. 2 is a front view of the implant assembly of FIG. 1 interposed between vertebral bodies.

With continued reference to FIG. 1, implant member 110 includes a body portion 130 and an attachment portion 170. Body portion 130 includes first and second surfaces 112, 114 that engage endplates of superior and inferior vertebral bodies 50, 52, respectively (FIG. 2). Each of first and second surfaces 112, 114 defines ridges 132 or similar projections to aid in securing implant member 110 to vertebral bodies 50, 52 for enhanced gripping of vertebral bodies 50, 52 and minimizing movement of implant member 110 relative to vertebral bodies 50, 52. In addition, body portion 130 includes first and second sidewalls 115, 117 that define the width of implant member 110. Body portion 130 defines a cavity 135 to accommodate bone graft material therein. In addition, body portion 130 may be tapered to facilitate insertion thereof into the intervertebral space and provide an amount of lordosis.

Attachment portion 170 includes a male dovetail joint 128A that extends along at least a portion of the width of attachment portion 170 between first and second sidewalls 115, 117. Attachment portion 170 defines guide portions 122 dimensioned to engage a bone screw 140 (FIG. 2). Each guide portion 122 defines a groove that leads into respective first and second surfaces 112, 114. In particular, each guide portion 122 provides a desired trajectory of bone screw 140 into respective vertebral body 50, 52, as will be described below.

Figure 1A:
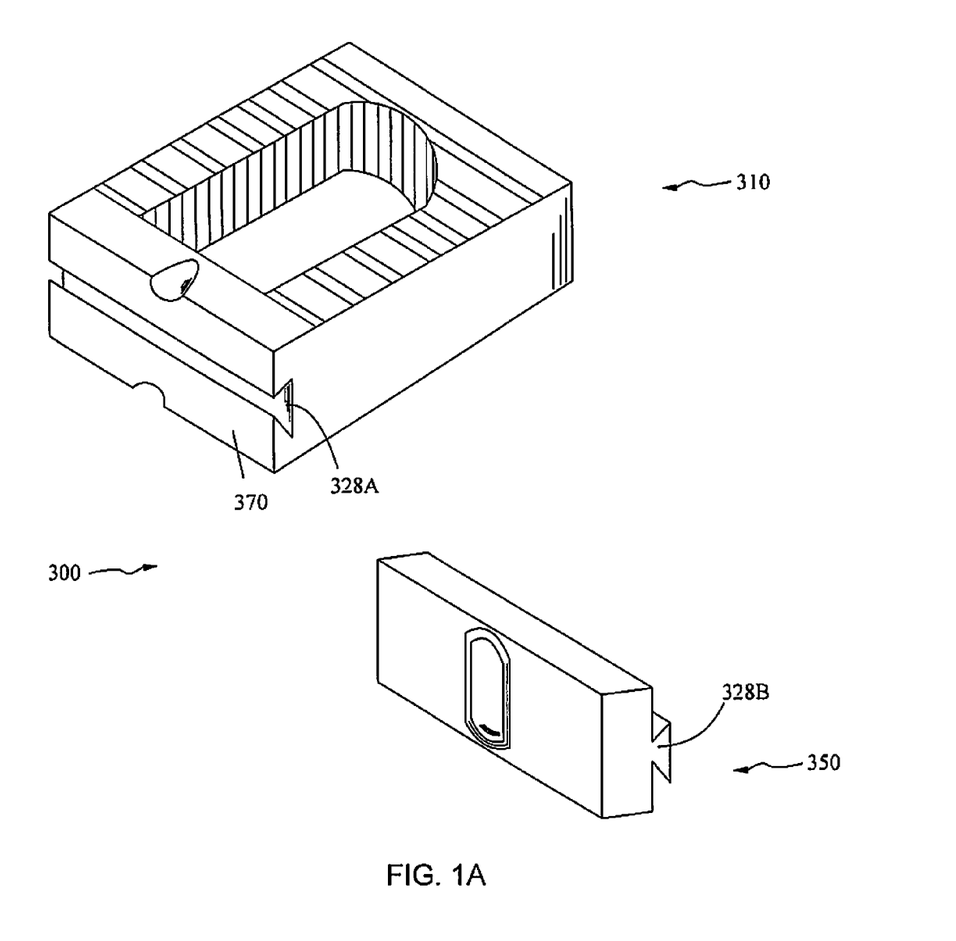
FIG. 1A is a perspective view of an intervertebral implant assembly in accordance with another embodiment of the present disclosure with parts separated.

With continued reference to FIG. 1, retention member 150 defines a female dovetail joint 128B substantially along the length thereof. Female dovetail joint 128B is dimensioned for slidably engaging the corresponding male dovetail joint 128A that extends between first and second sidewalls 115, 117. In this manner, implant member 110 and retention member 150 may be joined as a unitary construct. However, it is further contemplated that alternative mode of attachment such as, e.g., T-joints and alignment pins for frictional engagement with mating recesses, may be utilized to attach retention member 150 with implant member 110. It is also envisioned that in an embodiment, an intervertebral implant assembly 300 (FIG. 1A) includes an implant member 310 defining a female dovetail joint 328A in an attachment portion 370 of implant member 310 and a retention member 350 including a corresponding male dovetail joint 328B.

With reference back to FIG. 1, retention member 150 further defines an elongated access through hole 124 adapted and dimensioned to receive bone screws 140. In particular, access through hole 124 is defined by arcuate and dished curvilinear sidewalls, whereby the tightening of bone screws 140 within access through hole 124 forces the screw head and the arcuate and curvilinear sidewalls of access through hole 124 into locking engagement with one another when fully seated.

Figure 3:
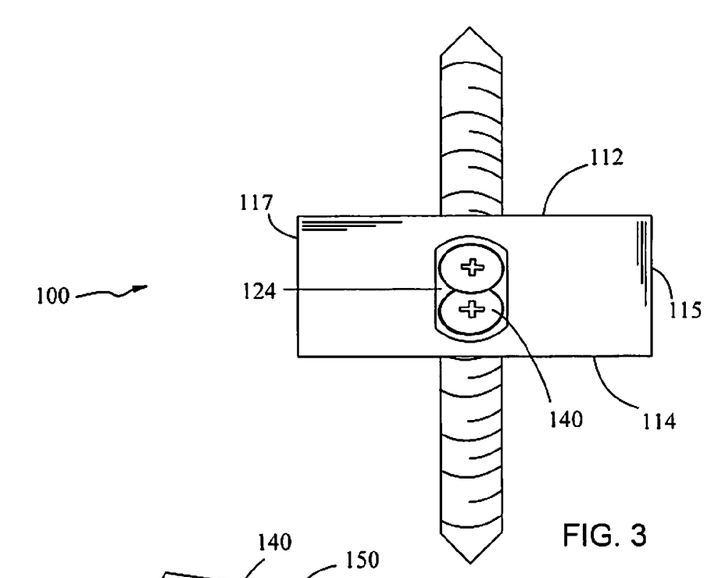
FIG. 3 is a front view of the implant assembly of FIG. 1 having bone screws inserted therethrough.
Figure 4:
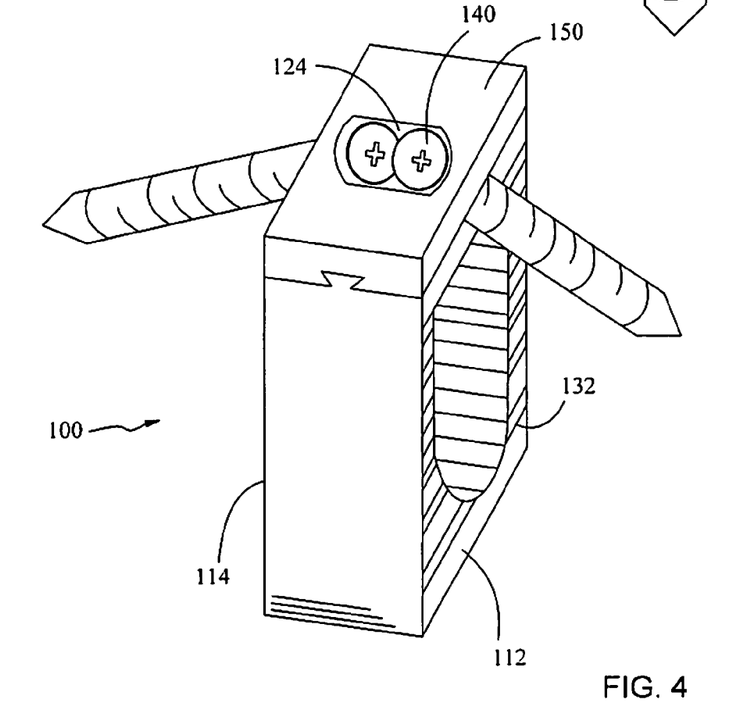
FIG. 4 is a perspective view of the implant assembly of FIG. 3.

With reference now to FIGS. 2-4, the arcuate and dished curvilinear sidewalls of access through hole 124 form a locking engagement with a pair of bone screws 140. In particular, one of bone screws 140 is driven into an inferior vertebral body 52 and the other bone screw 140 is driven into the superior vertebral body 50, as shown in phantom in FIG. 2. Specifically, bone screws 140 are first inserted through access through hole 124 and follow the respective trajectory delineated by guide portions 122 which facilitates insertion of bone screws 140 into respective inferior and superior vertebral bodies 50, 52. Under such configuration, bone screws 140 are in a single plane common to both the superior and inferior vertebral bodies 50, 52.

Figure 5:
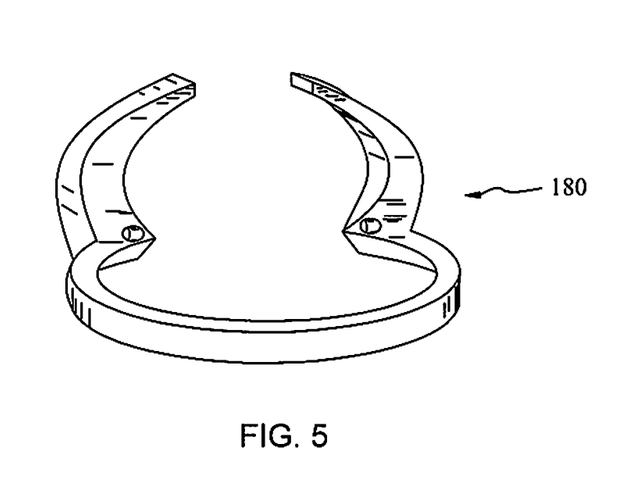
FIG. 5 is a perspective view of a bone screw retainer clip for use with the implant assembly of FIG. 1.
Figure 6:
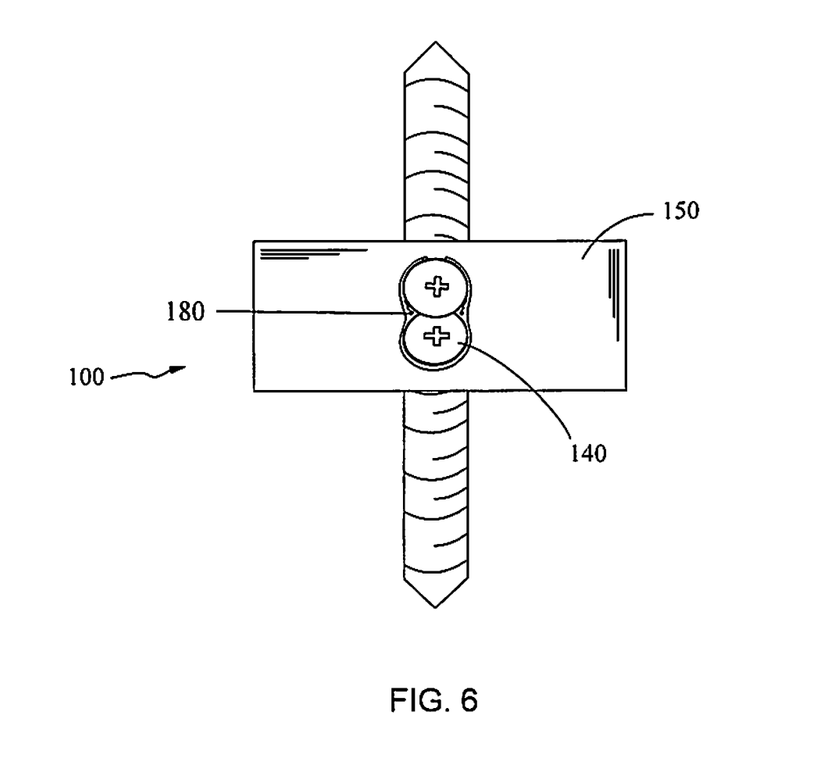
FIG. 6 is a front view of the implant assembly of FIG. 3 including the bone screw retainer clip of FIG. 5 mounted therein.

With reference now to FIGS. 5 and 6, a screw retainer clip 180 may be utilized as an additional safety measure to guard against bone screw 140 separation in the event of accidental loosening or breakage of bone screws 140. In particular, screw retainer clip 180 has a shape of a "bent open eight." Screw retainer clip 180 is placed in a pre-defined groove (not shown) in the periphery of the sidewalls of access through hole 124. Retainer clip 180 may be initially compressed by a tool and inserted into access through hole 124 to engage the pre-defined groove. Subsequent to compression of clip 180 and insertion into access through hole 124, retainer clip 180 and retention member 150 form a unitary assembly. Thereafter, each of bone screw 140 can be inserted individually in their respective apertures. Retainer clip 180 is designed to deflect and enable the heads of bone screws 140 to pass therethrough, and then return to its prior position to inhibit bone screw 140 from falling out of access through hole 124 should it become loosened.

Figure 7:
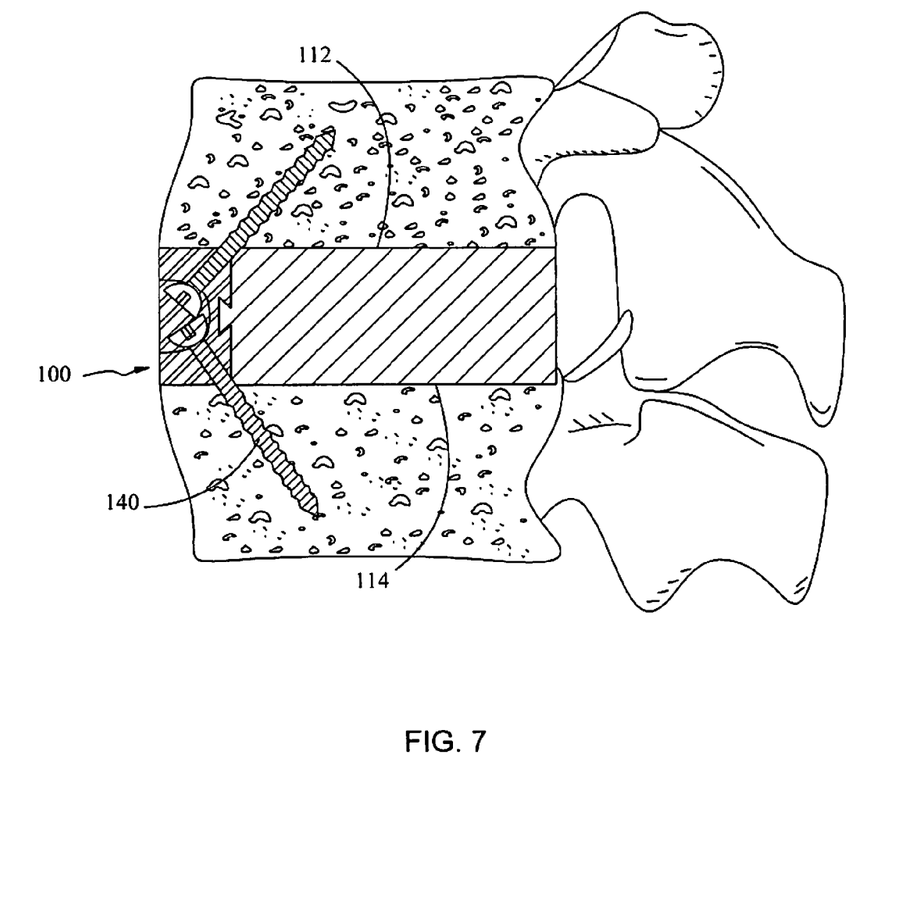
FIG. 7 is a longitudinal cross-sectional view of the implant assembly of FIG. 1 securely positioned between the vertebral bodies by the bone screws.

With reference now to FIG. 7, it is contemplated that bone screw 140 may include a spherical or semi-spherical head with a substantially flat upper surface, such that the spherical surface of one of the pair of bone screws 140 engages the top surface of the other of the pair of bone screws 140 regardless of the trajectory of the pair of bone screws 140. In this manner, a reliable head-to-head contact is achieved independent of bone screw 140 trajectories.

It is envisioned that access through hole 124 may further define an exit aperture (not shown). The exit aperture may be integrally defined with access through hole 124 or may be defined within a metallic insert that includes a spherical or semi-spherical curvilinear sidewall for each bone screw 140. Such configuration provides variation in bone screw 140 trajectory and increased contact between bone screw 140 and retention member 150.

In use, the surgeon first distracts vertebral bodies 50, 52 of interest to establish the intervertebral space. The surgeon may then remove vertebral tissue, if necessary or desired. At this time, the surgeon pairs implant member 110 with retention member 150 by sliding male dovetail joint 128A of implant member 110 through female dovetail joint 128B of retention member 150. Thereafter, the surgeon positions intervertebral implant assembly 100 between the desired vertebral bodies 50, 52. The surgeon secures intervertebral implant assembly 100 to vertebral bodies 50, 52 to inhibit expulsion or malpositioning by inserting a pair of bone screws 140 through access through hole 124 of retention member 150 and into the inferior and superior vertebral bodies 50, 52, respectively, via respective guide portions 122, as best illustrated in FIG. 7. In addition, the horizontal orientation of dovetail joints 128A, 128B inhibits relative longitudinal movement between implant member 110 and retention member 150 while implanted between vertebral bodies 50, 52.

Figure 8:
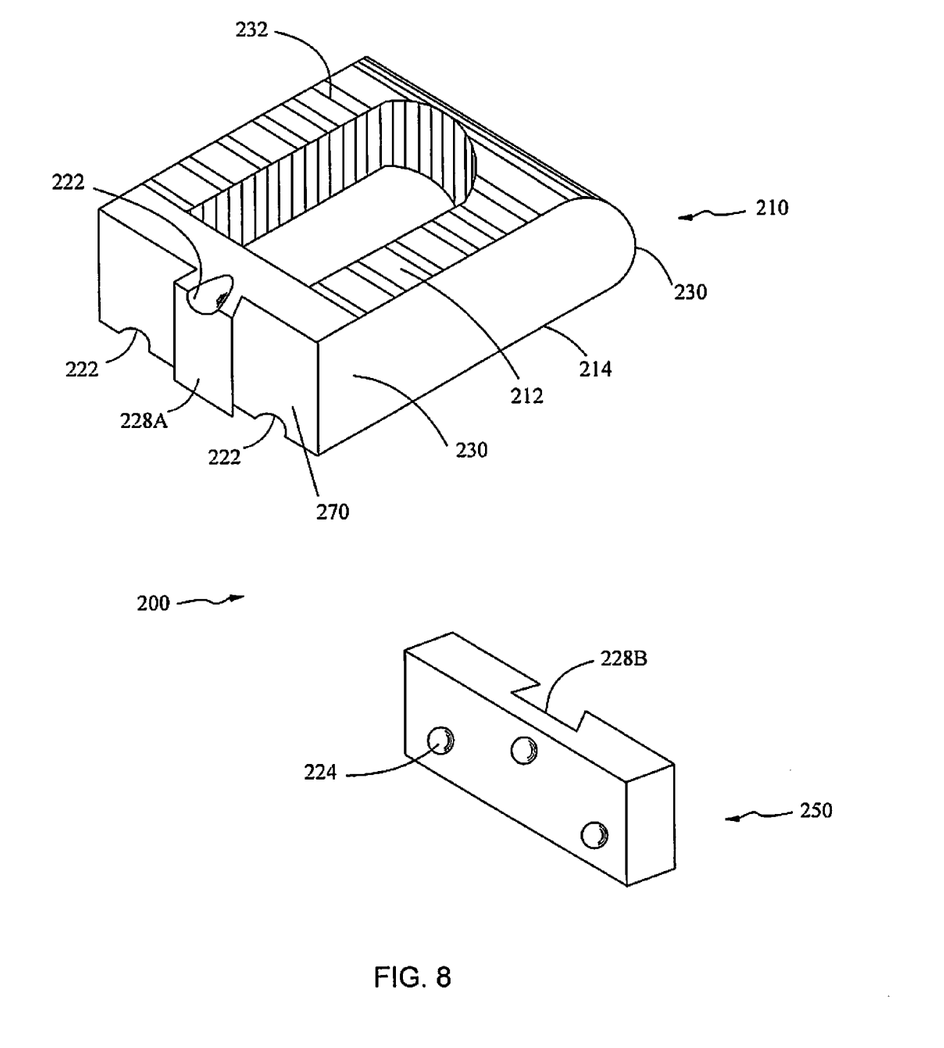
FIG. 8 is a perspective view of an intervertebral implant assembly in accordance with another embodiment of the present disclosure with parts separated.

With reference now to FIG. 8, another embodiment of an intervertebral implant assembly 200 is illustrated. In the interest of brevity, the present embodiment will focus on the differences between the previously described implant assembly 100 and implant assembly 200. Implant assembly 200 is configured and adapted to be positionable between vertebral bodies 50, 52 to support vertebral bodies 50, 52 and to promote spinal fusion. Implant assembly 200 includes an implant member 210 and a retention member 250.

With continued reference to FIG. 8, implant member 210 includes a body portion 230 and an attachment portion 270. Body portion 230 includes first and second surfaces 212, 214 that engage endplates of the superior and inferior vertebral bodies 50, 52, respectively. Each of first and second surfaces 212, 214 includes ridges 232 or similar projections to aid in securing implant member 210 to vertebral bodies 50, 52 for enhanced gripping of vertebral bodies 50, 52 and minimizing movement of implant member 210 relative to vertebral bodies 50, 52.

Attachment portion 270 includes a male dovetail joint 228A and defines guide portions 222 dimensioned to engage bone screw 140. In particular, a single guide portion 222 is defined in male dovetail joint 228A such that the single guide portion 222 leads into first surface 212. In addition, a pair of guide portions 222 adjacent male dovetail joint 228A is defined in attachment portion 270 such that the pair of guide portions 222 leads into second surface 214. Each guide portion 222 defines a groove providing a desired trajectory of bone screws 140 into respective vertebral bodies 50, 52. Accordingly, under such configuration, a single bone screw 140 is driven into a superior vertebral body 50 and a pair of bone screws 140 is driven into the inferior vertebral body 50.

Figure 8A:
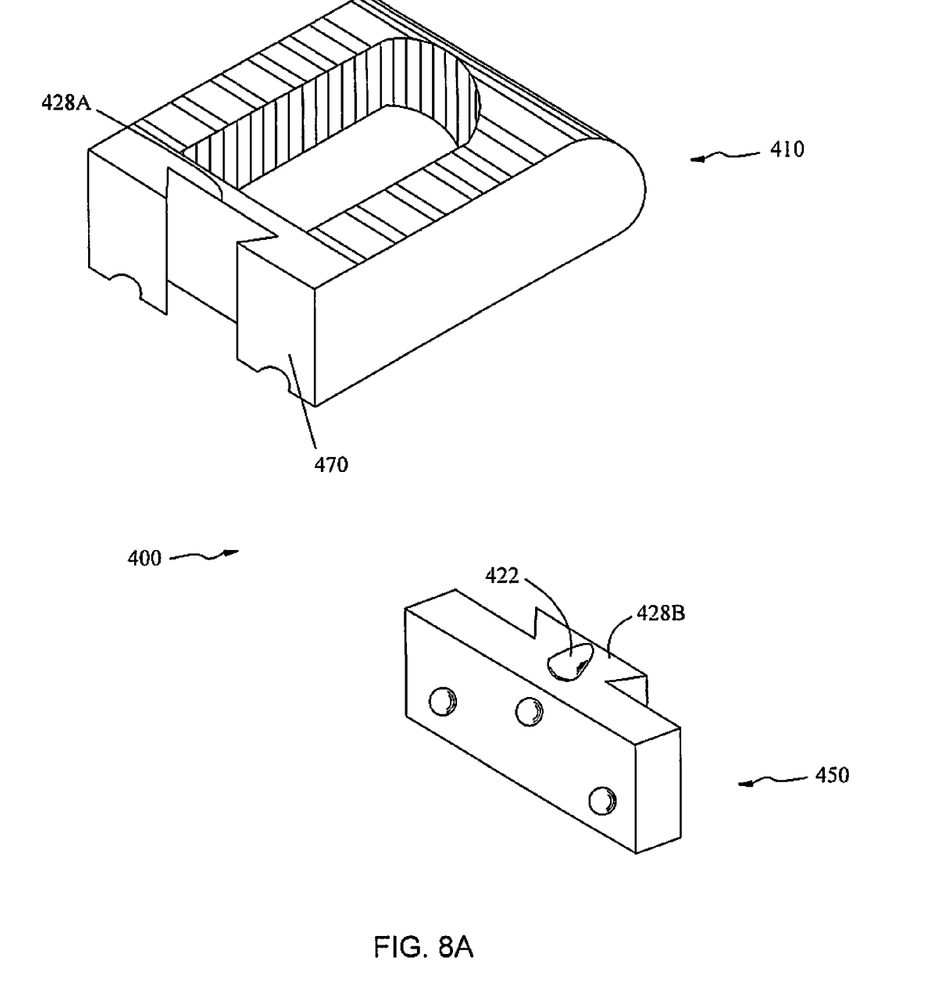
FIG. 8A is a perspective view of an intervertebral implant assembly in accordance with another embodiment of the present disclosure with parts separated.

With continued reference to FIG. 8, retention member 250 defines a female dovetail joint 228B. In contrast to female dovetail joint 128B of implant assembly 100, female dovetail joint 228B is defined along the width of retention member 250. Female dovetail joint 228B is dimensioned to slidably engage the corresponding male dovetail joint 228A of attachment portion 270. In this manner, implant member 210 and retention member 250 may be joined as a unitary construct. However, it is further contemplated that alternative mode of attachment such as, e.g., T-joint and alignment pins for frictional engagement with mating recesses, may be utilized to couple retention member 250 with implant member 210. It is also envisioned that in an embodiment, an intervertebral implant assembly 400 (FIG. 8A) includes an implant member 410 defining a female dovetail joint 428A in an attachment portion 470 of implant member 410 and a retention member 450 including a corresponding male dovetail joint 428B. In particular, male dovetail joint 428B defines a guide portion 422 dimensioned to engage bone screw 140.

With reference back to FIG. 8, in contrast to retention member 150 of implant assembly 100, retention member 250 defines a plurality of access through holes 224 adapted and dimensioned to receive therethrough bone screws 140. Each access through hole 224 is dimensioned to receive a single bone screw 140. Each through hole 224 is defined by arcuate and dished curvilinear sidewalls, whereby the tightening of the bone screw 140 within access through hole 224 forces the screw head and the arcuate and curvilinear sidewalls of access through hole 124 into locking engagement with one another when fully seated. Each access through hole 224 corresponds to a single guide portion 222. Each access through hole 224 is in communication with guide portions 222 such that bone screw 140 inserted through access through hole 224 is guided into respective vertebral bodies 50, 52 by guide portions 222 providing the desired trajectory of bone screws 140 into respective vertebral bodies 50, 52. In particular, one guide portion 222 leads into first surface 212 and a pair of guide members 222 leads into second surface 214.

It is contemplated that any number of bores 224, guide portions 222, and bone screws 140 may be utilized to meet the need of a particular surgical procedure being performed. It is further envisioned that access through hole 224 may be threaded or smooth. The head of bone screws 140 may also may be threaded or smooth. In addition, bone screws 140 may be made of a material that is harder than the material of the sidewalls that define access through hole 224 and/or the metallic insert that defines the exit aperture. For example, bone screw 140 may be made of titanium alloy (e.g., Ti-6Al-4V) and the sidewalls and/or the metallic insert may be made of a relatively softer compatible material, such as a softer titanium material (e.g. commercially pure titanium). Under such configuration, as bone screw 140 is advanced through access through hole 224 and/or the exit aperture thread of bone screw 140 deforms the sidewalls and/or the metallic insert and secures bone screw 140 therewith to inhibit loosening of bone screw 140. This type of screw locking arrangement is described in U.S. Pat. No. 6,322,562 to Wolter, which is incorporated by reference herein in its entirety.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. An intervertebral implant assembly comprising:
   an implant member including a body portion and an attaching portion on a proximal face of the implant member, the body portion including first and second surfaces adapted to engage first and second vertebral bodies, respectively, the attaching portion including a male dovetail joint extending longitudinally on the proximal face of the implant member; and
   a retention member detachably coupled to the attaching portion of the implant member, the retention member defining a female dovetail joint corresponding to the male dovetail joint of the attaching portion, the retention member defining an access bore configured and dimensioned to receive a bone screw therein, wherein the proximal face of the implant member defines a first guide portion that leads into the first surface, whereby when the bone screw is inserted through the access bore the bone screw is directed towards the first vertebral body through the first guide portion.

2. The intervertebral implant assembly according to claim 1, wherein the access bore is defined by arcuate and dished curvilinear sidewalls.

3. The intervertebral implant assembly according to claim 1, wherein the attaching portion further defines a second guide portion, the first and second guide portions leading into the first and second surfaces, respectively.

4. The intervertebral implant assembly according to claim 3, wherein the access bore is adapted and dimensioned to receive a pair of bone screws therein, whereby the pair of bone screws is inserted into the first and second vertebral bodies through the first and second guide portions, respectively.

5. The intervertebral implant assembly according to claim 4, wherein head portions of the pair of bone screws lockingly engage each other in the access bore.

6. The intervertebral implant assembly according to claim 3, wherein the first and second guide portions are each defined in a peripheral portion of the attaching member.

7. The intervertebral implant assembly according to claim 6, wherein the bone screw includes thread below a seat surface of the bone screw, whereby the thread deforms a portion of the sidewall of the access bore.

8. The intervertebral implant assembly according to claim 1, further comprising a pair of bone screws, wherein the access bore is adapted and dimensioned to receive the pair of bone screws.

9. The intervertebral implant assembly according to claim 8, wherein one of the pair of bone screws inserted through the access bore is secured to the first vertebral body through the first guide portion, and the other of the pair of bone screws is secured to the second vertebral body through the second guide portion.

10. The intervertebral implant assembly according to claim 1, wherein the body portion is tapered along the length thereof.

11. The intervertebral implant assembly according to claim 1, wherein the first and second surfaces define projections to aid in securing the implant assembly between the vertebral bodies.

12. The intervertebral implant assembly according to claim 1, wherein the body portion defines a cavity.

13. The intervertebral implant assembly according to claim 1, wherein the attaching portion of the implant member further defines second and third guide portions adjacent the male dovetail joint, the second and third guide portions leading into the second surface.

14. The intervertebral implant assembly according to claim 13, wherein the retention member further defines a plurality of access bores corresponding to the first, second and third guide portions of the implant member.

15. The intervertebral implant assembly according to claim 1, wherein the implant member further includes first and second sidewalls, the male dovetail joint extending along at least a portion of the width of the implant member between the first and second sidewalls.

16. The intervertebral implant assembly according to claim 15, wherein the female dovetail joint is defined along the length of the retention member, the female dovetail joint corresponding to the male dovetail joint disposed between the first and second sidewalls of the implant member.

17. The intervertebral implant assembly according to claim 1, further comprising a retention clip disposed within the access bore of the retention member to retain the bone screws therein.

18. The intervertebral implant assembly according to claim 1, wherein the retention member is slidably detachable from the implant member.

19. The intervertebral implant assembly according to claim 1, wherein the first guide portion is oriented substantially orthogonal to the male dovetail joint.

20. The intervertebral implant assembly according to claim 1, wherein the male dovetail joint extends along a majority of a length of the proximal face.

21. A method of securing adjacent vertebral bodies, comprising:
   providing an intervertebral implant assembly including:
      an implant member including a body portion and an attaching portion on a proximal face of the implant member, the body portion including first and second surfaces adapted to engage first and second vertebral bodies, respectively, the attaching portion including a male dovetail joint extending longitudinally on the proximal face of the implant member, the proximal face of the implant member defining a first guide portion that leads into the first surface; and
      a retention member detachably coupled to the attaching portion of the implant member, the retention member defining a female dovetail joint corresponding to the male dovetail joint of the attaching portion and an access bore configured and dimensioned to receive therein a pair of bone screws, whereby when one of the pair of bone screws is inserted through the access bore, the one of the pair of bone screws is directed towards the first vertebral body through the first guide portion;
   distracting adjacent vertebral bodies;
   inserting the intervertebral implant assembly between the first and second vertebral bodies; and
   inserting the pair of bone screws through the retention member and into the respective vertebral bodies.

22. The method according to claim 21, further comprising removing vertebral tissue.

23. The method according to claim 21, wherein the intervertebral implant assembly further includes a retainer clip disposed within the access bore.

24. The method according to claim 21, wherein the retainer clip has a bent open eight shape.

25. The method according to claim 21, wherein the attaching portion further defines a second guide portion that leads into the second surface.

26. The method according to claim 25, wherein inserting the pair of bone screws through the retention member and into the respective vertebral bodies includes inserting the pair of bone screws through the access bore and into the first and second vertebral bodies through the first and second guide portions, respectively.

* * * * *